(12) United States Patent
Watling et al.

(10) Patent No.: US 10,351,675 B2
(45) Date of Patent: Jul. 16, 2019

(54) COMPOSITIONS AND METHODS FOR INJECTABLE COMPOSITION FOR AN ACCOMMODATING INSTRAOCULAR LENS

(71) Applicant: Brien Holden Vision Institute, Sydney, New South Wales (AU)

(72) Inventors: Jason Watling, Sydney (AU); Stephen Clarke, Mawson Lakes (AU); Kim-Anh Thi Nguyen, Mawson Lakes (AU); Tony Aitchison, Mawson Lakes (AU); Elda Markovic, Morphettville (AU); Anton Blencowe, Adelaide (AU); Chun Kit Lo, Sydney (AU)

(73) Assignee: Adventus Technology, Inc., Irvine, CA (US)

(*) Notice: Subject to any disclaimer, the term of this patent is extended or adjusted under 35 U.S.C. 154(b) by 0 days.

(21) Appl. No.: 15/535,671

(22) PCT Filed: Dec. 21, 2015

(86) PCT No.: PCT/AU2015/050821
§ 371 (c)(1),
(2) Date: Jun. 13, 2017

(87) PCT Pub. No.: WO2016/101025
PCT Pub. Date: Jun. 30, 2016

(65) Prior Publication Data
US 2018/0273687 A1   Sep. 27, 2018

Related U.S. Application Data

(60) Provisional application No. 62/095,387, filed on Dec. 22, 2014.

(51) Int. Cl.
| | | |
|---|---|---|
| *C08G 77/12* | (2006.01) | |
| *A61K 31/695* | (2006.01) | |
| *C08L 83/06* | (2006.01) | |
| *C08G 77/14* | (2006.01) | |
| *C08G 77/16* | (2006.01) | |
| *C08L 83/04* | (2006.01) | |
| *A61L 27/18* | (2006.01) | |
| *C08G 77/18* | (2006.01) | |
| *C08G 77/20* | (2006.01) | |
| *A61F 2/16* | (2006.01) | |

(52) U.S. Cl.
CPC ............ *C08G 77/12* (2013.01); *A61K 31/695* (2013.01); *A61L 27/18* (2013.01); *C08G 77/14* (2013.01); *C08G 77/16* (2013.01); *C08G 77/18* (2013.01); *C08G 77/20* (2013.01); *C08L 83/04* (2013.01); *C08L 83/06* (2013.01); *A61F 2/1624* (2013.01); *A61F 2240/001* (2013.01)

(58) Field of Classification Search
CPC ................................ C08G 77/18; C08G 77/16
See application file for complete search history.

(56) References Cited

U.S. PATENT DOCUMENTS

| | | | | |
|---|---|---|---|---|
| 2,803,690 | A | * | 8/1957 | Stevens ................. H01M 10/02 429/126 |
| 4,608,050 | A | | 8/1986 | Wright et al. |
| 6,066,172 | A | * | 5/2000 | Huo ........................ A61L 27/18 264/1.1 |
| 7,776,351 | B2 | | 8/2010 | Benz |
| 2001/0047162 | A1 | | 11/2001 | Yugari |
| 2002/0167735 | A1 | | 11/2002 | Jethmalani et al. |
| 2006/0135477 | A1 | | 6/2006 | Haitjema et al. |
| 2011/0190467 | A1 | | 8/2011 | Hughes et al. |
| 2013/0331476 | A1 | * | 12/2013 | Bae ...................... C09D 183/06 522/148 |

FOREIGN PATENT DOCUMENTS

EP       1272233       8/2005

OTHER PUBLICATIONS

Odian (Principles of Polymerization, 4th Ed., (2004) pp. 19-24).*
Takahashi (Polymer Journal, 40(5) 465-474 (2008)).*
International Search Report dated May 7, 2016 for PCT/AU2015/050821.

* cited by examiner

Primary Examiner — Kuo Liang Peng
(74) Attorney, Agent, or Firm — Jones Day

(57) ABSTRACT

The present disclosure relates to injectable compositions and methods of making injectable compositions of moisture curing siloxane polymers for forming accommodating intraocular lenses. In certain embodiments, the moisture curing siloxane polymers are comprised of an organosilicon compound and a hydrolytically sensitive siloxane moiety and have a specific gravity of greater than about 0.95, a number average molecular weight (Mn) greater than about 5,000 or about 20,000 and a weight average molecular weight (Mw) greater than about 20,000 or about 40,000. The disclosure includes accommodating intraocular lenses formed from moisture curing siloxane polymers and having a modulus of elasticity of less than about 6 kPa, less than 20% post-cure extractables, refractive index ranging from 1.4 to 1.5 and dioptric range of accommodation of 0D to 10D.

11 Claims, No Drawings

COMPOSITIONS AND METHODS FOR INJECTABLE COMPOSITION FOR AN ACCOMMODATING INSTRAOCULAR LENS

CROSS REFERENCE TO RELATED APPLICATION

This application is the National Phase application of International Application No. PCT/AU2015/050821, filed Dec. 21, 2015, which designates the United States and was published in English, which claims the benefit of U.S. Provisional Application No. 62/095,387, filed Dec. 22, 2014. These applications, in their entirety, are incorporated herein by reference.

This application is also related to U.S. Pat. No. 7,001,426 entitled "One-Piece Minicapsulorhexis Valve" and U.S. Pat. No. 6,358,279 entitled "Minicapsulorhexis Valve." Each of these patents are incorporated herein by reference in their entirety.

FIELD

The present disclosure relates to compositions using moisture curing siloxane polymers for forming accommodating intraocular lenses, for example, in situ. The disclosure also relates to compositions and/or methods of making injectable compositions for forming accommodating intraocular lenses using moisture curing siloxane polymers as well as methods of forming accommodating intraocular lenses, for example, in situ (in the eye of a warm blooded animal).

BACKGROUND

Accommodation is the ability of the eye to change the power of the eye to enable clear vision with objects in focus for a range of distances. With a change in focus from distance to near vision, the ciliary muscle contracts, the zonules (filaments that connect the crystalline lens to the ciliary muscle) relax and the crystalline lens takes a more rounded form resulting in an increase in power and resulting in the ability of the eye to focus on near objects. However, with age, there is a gradual decline in the accommodative power of the eye due to the crystalline lens losing its flexibility in changing its shape and in humans, in their forties this results in blurred vision for near tasks such as reading and is called Presbyopia. The condition is commonly managed with glasses or contact lenses.

In those that have cataracts, the crystalline lens is extracted and an intraocular lens is commonly implanted. Typically, the intraocular lens is a fixed focus lens that enables the eye to see distant objects. Since the implanted lens is unable to change shape and thus a change in power, the condition typically necessitates the use of spectacle lenses to be able to see at near. In both these situations, i.e. in presbyopia and following cataract extraction, the desire is to eliminate or reduce the need for spectacles for near distances and restore the accommodative power i.e. the re-establishment of the eye's ability to focus for a range of distances.

While many approaches have been explored, the development of a flexible material that would replace the natural material of the crystalline lens and fill the capsular bag and provide accommodation is highly desired. For example, two part silicone elastomers (referred to as RTV or LTV silicones) require a polyfunctional vinyl siloxane as one component and a polyfunctional hydrosiloxane silicone polymer as the other component and cure at body temperature via platinum catalysed hydrosilation reaction. However, these compositions suffer from the need to mix the two polymers immediately prior to injection and introduced into the capsular bag before the viscosity of the composition rises too far. Another approach is based on use of compositions of polysiloxanes with photocurable moieties, however it has been said that the modulus of the cured composition is too high to restore accommodation. Another approach involves hydrogel compositions that offer access to low modulus compositions but involve UV curing that poses a problem with respect to their safety for surrounding tissues. Also the resultant cured composition did not achieve the desired refractive index to provide for the accommodative power and also suffered from post cure swelling.

Thus there is a continued demand for compositions and methods that are disclosed herein. For example, compositions suitable for injection into the capsular bag of the eye of a warm blooded animal and are able to be cured in situ and allow for restoration of accommodative power.

Reference to prior art in this specification is not, and should not be taken as acknowledgement or form of suggestion that this prior art forms part of the general knowledge in Australia or other jurisdictions or that this prior art could reasonably be expected to be ascertained, understood and regarded as relevant by person skilled in the art.

SUMMARY

Certain embodiments are directed to an injectable composition comprising an organosilicon compound and a hydrolytically sensitive siloxane moiety to form an accommodating intraocular lens in situ in the capsular bag of an eye of a warm blooded animal (for example, a human patient). Certain embodiments are directed to an injectable composition comprising an organosilicon compound and a hydrolytically sensitive siloxane moiety to form an accommodating intraocular lens for use in an eye of a human patient. Certain embodiments are directed to an injectable composition comprising an organosilicon compound and a hydrolytically sensitive siloxane moiety that when introduced into the capsular bag of an eye of a warm blooded animal, the composition substantially cures in situ upon contact with one or more of the following: moisture, water and/or an aqueous medium to form an accommodating intraocular lens. The result is a substantially cured composition that forms an intraocular lens that is suitably transparent and a refractive index that is suitably close to or greater than that of a natural crystalline lens. Moreover, the substantially cured composition may have a modulus of elasticity in a range that may be capable of deforming with the stretching and relaxing forces on the capsular bag from the ciliary muscle via the zonules. The deformation of the intraocular lens may result in a change of the power of the eye and thus accommodation.

Certain embodiments are directed to an injectable composition comprising an organosilicon compound and a hydrolytically sensitive siloxane moiety with a specific gravity greater than about 0.95 and the injectable composition is substantially cured in situ upon contact with moisture, water and/or an aqueous medium to form an accommodating intraocular lens. In certain embodiments, the organosilicon compound comprises linear polysiloxane polymer chains, polysiloxane copolymer chains, branched polysiloxane polymer chains, or combinations thereof. In certain embodiments, the hydrolytically sensitive siloxane moiety comprises one or more silane ether and silane ester groups. In certain embodiments, the specific gravity of the composition prior to curing would typically be sufficient to enable filling of the capsular bag without the composition floating on top of the aqueous medium. In certain embodiments, the specific gravity is about 0.96 to 1.06. In other embodiments, the specific gravity is 0.97 to 1.05, 0.98 to 1.05, 0.99 to 1.05, 1 to 1.04, 1 to 1.05, 1.1 to 1.5, about 1.2 to 1.5 or about 1.3 to 1.5.

Certain embodiments are directed to an injectable composition comprising an organosilicon compound and a hydrolytically sensitive siloxane moiety with a specific gravity greater than about 0.95, the number average molecular weight ($M_n$) of the injectable composition is greater than about 20,000 and the injectable composition is substantially cured in situ upon contact with moisture, water and/or an aqueous medium to form an accommodating intraocular lens.

Certain embodiments are directed to an injectable composition comprising an organosilicon compound and a hydrolytically sensitive siloxane moiety with a specific gravity greater than about 0.95, the number average molecular weight ($M_e$) of the injectable composition is greater than about 5,000, and the injectable composition is substantially cured in situ upon contact with moisture, water and/or an aqueous medium to form an accommodating intraocular lens.

Certain embodiments are directed to an injectable composition comprising an organosilicon compound and a hydrolytically sensitive siloxane moiety with a specific gravity greater than about 0.95, the number average molecular weight ($M_n$) of the injectable composition is greater than about 20,000, the weight average molecular weight ($M_w$) of the injectable composition is greater than about 40,000 and the injectable composition is substantially cured in situ upon contact with moisture, water and/or an aqueous medium to form an accommodating intraocular lens.

Certain embodiments are directed to an injectable composition comprising an organosilicon compound and a hydrolytically sensitive siloxane moiety with a specific gravity greater than about 0.95, the number average molecular weight ($M_n$) of the injectable composition is greater than about 5,000, the weight average molecular weight ($M_w$) of the injectable composition is greater than about 20,000 and the injectable composition is substantially cured in situ upon contact with moisture, water and/or an aqueous medium to form an accommodating intraocular lens.

In other embodiments, the $M_n$ of the injectable composition is 20,000 to 150,000, 20,000 to 140,000, 20,000 to 120,000, 20,000 to 100,000, 20,000 to 80,000, 20,000 to 60,000, 20,000 to 40,000, 5,000 to 20,000 or 5,000 to 10,000. In other embodiments, the $M_n$ of the injectable composition is at least about 5,000, at least about 10,000, at least about 20,000, at least about 40,000, at least about 60,000, at least about 80,000 or at least about 100,000. In other embodiments, the weight average molecular weight ($M_w$) of the injectable composition is greater than about 40,000. In certain embodiments, the weight average molecular weight ($M_w$) of the injectable composition is between about 40,000 to about 300,000, about 40,000 to about 250,000, about 40,000 to about 200,000, about 40,000 to about 150,000, about 40,000 to about 100,000, 20,000 to about 50,000. In certain embodiments, the weight average molecular weight ($M_w$) of the injectable composition is at least 20,000, at least about 40,000, at least about 80,000, at least about 120,000, at least about 160,000, at least about 200,000, at least about 240,000 and at least about 280,000. In other embodiments, the $M_n$ of the injectable composition is 5,000 to 150,000, 5,000 to 140,000, 5,000 to 120,000, 5,000 to 100,000, 5,000 to 80,000, 5,000 to 60,000 or 5,000 to 40,000. In other embodiments, the weight average molecular weight ($M_w$) of the injectable composition is greater than about 20,000. In certain embodiments, the weight average molecular weight ($M_w$) of the injectable composition is between about 20,000 to about 300,000, about 20,000 to about 250,000, about 20,000 to about 200,000, about 20,000 to about 150,000 or about 20,000 to about 100,000.

Certain embodiments are directed to an injectable composition comprising an organosilicon compound and a hydrolytically sensitive siloxane moiety with a viscosity suitable for injection through an injection device. In certain embodiments, the viscosity of the injectable composition is at least about 0.5 Pa·s. In other embodiments, the viscosity of the injectable composition is between about 0.5 to 30 Pa·s, 0.5 to 25 Pa·s, 0.5 to 20 Pa·s, 0.5 to 15 Pa·s, 0.5 to 10 Pa·s and 0.5 to 5 Pa·s. Certain embodiments are directed to an injectable composition comprising an organosilicon compound and a hydrolytically sensitive siloxane moiety with a specific gravity greater than about 0.95, the number average molecular weight ($M_n$)) between 20,000 to 150,000, the weight average molecular weight ($M_w$) between 40,000 to 300,000, viscosity of about 0.5 to 30 Pa·s and is substantially cured in situ upon contact with moisture, water and/or an aqueous medium to form an accommodating intraocular lens.

Certain embodiments are directed to an injectable composition comprising an organosilicon compound and a hydrolytically sensitive siloxane moiety with a specific gravity greater than about 0.95, the number average molecular weight ($M_n$) between 5,000 to 150,000, the weight average molecular weight ($M_w$) between 20,000 to 300,000, viscosity of about 0.5 to 30 Pa·s and is substantially cured in situ upon contact with moisture, water and/or an aqueous medium to form an accommodating intraocular lens.

In certain embodiments, to obtain a substantially cured composition, the mole fraction of the end groups that possess a hydrolysable and cross linkable moiety is between about 20% to about 100%. In other embodiments, the mole fraction of the end groups that possess a hydrolysable and cross linkable moiety of the injectable composition is at least about 20%. In other embodiments, the mole fraction of the end groups that possess a hydrolysable and cross linkable moiety of the injectable composition is between 20% to 95%, 20% to 90%, 20% to 85%, 20% to 80%, 20% to 75%, 20% to 70% and 20% to 65%, 20% to 60%, 20% to 55%, 20% to 50%, 20% to 45%, 20% to 40%, 20% to 35%, 20% to 30% and 20% to 25%. In other embodiments, the mole fraction of the end groups that possess a hydrolysable and cross linkable moiety of the injectable composition is at least about 95%, about 90%, about 85%, about 80%, about 75%, about 70%, about 65%, about 60%, about 55%, about 50%, about 45%, about 40%, about 35%, about 30%, about 25% and about 20%.

Certain embodiments are to a method of making an injectable composition for forming an accommodating intraocular lens in situ, comprising the step of mixing together an organosilicon compound and a hydrolytically sensitive siloxane moiety using catalytic hydrosilylation or condensation reaction to form a one-part injectable composition. In certain embodiments, the organosilicon compound may comprise linear polysiloxane polymer chains, polysiloxane copolymer chains, branched polysiloxane polymer chains, or combinations thereof. In certain embodiments, the organosilicon compound may include hydride terminated polydimethylsiloxane polymer chains or vinyl terminated polydimethylsiloxane polymer chains. In other embodiments, the organosilicon compound may include polyphenyl-methyl siloxane or polydiphenylsiloxane. In other embodiments, the hydrolytically sensitive siloxane moiety may comprise one or more of silyl ester groups or one of more silyl ether groups. In other embodiments, the hydrolytically sensitive siloxane moiety may include one or more of the following: for hydride terminated polymer chains: diethoxymethylvinylsilane, methyldiethoxyvinylsilane, triethoxyvinylsilane, dimethyldimethoxysilane, vinyldiacetoxymethylsilane, vinyldimethylacetoxysilane and allytriethoxysilane; for vinyl terminated polymer chains: diethoxymethylsilane, diacetoxymethylsilane, dimethylethoxysilane, dimethylacetoxysilane and triethoxysilane. The compounds may be synthesised by using methods that are known or obtained commercially for example from Gelest, Inc (PA, USA). In certain embodiments, the catalytic hydrosilation may be performed using one or more of catalysts including chloroplatinic acid, Karstedt's catalyst, Palladium acetate and Platinum Oxide. In certain embodiments where the hydrolytically sensitive siloxane moiety may be introduced through a condensation reaction, polymer macromonomers with silanol end groups may be condensed with polyfunctional silyl ester and silyl ether monomers such as tetraethylorthosilicate, methyltrimethoxysilane or methyltriacetoxysilane.

Certain embodiments relate to an accommodating intraocular lens formed in situ in the eye of a warm blooded animal by injecting a composition comprising an organosilicon compound and a hydrolytically sensitive siloxane moiety into the capsular bag of the eye of a warm blooded animal and allowing the composition to cure substantially upon contact with moisture, water or an aqueous medium to form the intraocular lens. The accommodating intraocular lens formed in situ may have certain properties or combination of properties. In certain embodiments, to be able to change shape and thus power and accommodative power of the eye, the modulus of the substantially cured composition is at least 6 kPa. In other embodiments, the modulus of elasticity is between 0.1 to 6 kPa, 0.1 to 5 kPa, 0.1 to 4 kPa, 0.1 to 3 kPa, 0.1 to 2 kPa, 2 to 6 kPa, 2 to 5 kPa, 2 to 4 kPa, 2 to 3 kPa, at least 2 kPa or at least 0.1 to 2 kPa.

In certain embodiments, the refractive index of the substantially cured composition ranges from about 1.4 to about 1.5. In certain embodiments, the refractive index is at least 1.4. To obtain the substantially cured composition with the desired refractive index, the proportion of the organosilicon compound and the hydrolytically sensitive siloxane moiety may be varied. In certain embodiments, the organosilicon compound may include polyphenyl-methyl siloxane or polydiphenylsiloxane to have a refractive index greater than about 1.41. In other embodiments, the refractive index is between 1.4 to 1.5, 1.4 to 1.48, 1.4 to 1.46, 1.4 to 1.44, 1.4 to 1.43, 1.4 to 1.42, 1.42 to 1.44, at least 1.41 or at least 1.42.

In certain embodiments, the extractables from the substantially cured composition is less than about 20%. In other embodiments, the extractables from the substantially cured composition is from about 0.5% to about 15% or about 0.5% to about 10%. In the other embodiments, the extractables from the substantially cured composition is between 0.5 to 20%, 0.5 to 18%, 0.5 to 16%, 0.5 to 14%, 0.5 to 12% 0.5 to 10%, 0.5 to 8%, 0.5 to 7%, 0.5% to 6%, 0.5 to 5%, 1 to 4%, 1 to 5%, 1 to 7%, 1 to 8%, 1 to 10%, 1 to 12%, 1 to 14%, 1 to 16%, 1 to 18%, less than 20%, less than 15%, less than 12%, less than 10%, less than 8%, less than 6%, less than 4% or less than 2%. In certain embodiments, at least 50% the extractables from the substantially cured composition have number average molecular weight ($M_n$) greater than about 30,000. In certain embodiments, at least 50% of the extractables from the substantially cured composition have number average molecular weight ($M_n$) greater than about 10,000. In other embodiments, the percent of extractables from the cured composition with $M_n$ greater than 30,000 is at least 30 to 55%, 35 to 55%, 40 to 55%, 45 to 55%, at least 55% or at least 45%. In other embodiments, the percent of extractables from the cured composition with $M_n$ greater than 10,000 is at least 30 to 55%, 35 to 55%, 40 to 55%, 45 to 55%, at least 55% or at least 45%. In certain embodiments, at least 50% of the extractables from the substantially cured composition have number average molecular weight ($M_n$) greater than 10,000, greater than 20,000, greater than 25,000 or greater than 35,000. In other embodiments, the substantially cured composition has a dioptric range of accommodation of 0.5D to 10D, 0.5D to 8D, 0.5D to 6D, 0.5D to 5D, 0.5D to 4 D, 0.5D to 3D, 1D to 2 D, at least 1D, at least 2D, at least 3D or at least 4D. In other embodiments, the substantially cured composition has a dioptric range of accommodation of 0D to 10D, 0D to 8D, 0D to 6D, 0D to 5D, 0D to 4 D, 0D to 3D, 0D to 2D, 0D to 1D, up to 1D, up to 2D, up to 3D, up to 4D, up to 5D, up to 6D, up to 7D, up to 8D, up to 9D and up to 10D. The dioptric range of accommodation of the substantially cured composition may be measured using suitable techniques, such as the Ex Vivo Accommodation Simulator (EVAS). In certain embodiments, the substantially cured composition is suitably transparent. In certain embodiments, the substantially cured composition permits about 80% or more of visible light to be transmitted. In other embodiments, the range of visible light that is transmitted ranges from about 80% to about 95%, 80% to 90%, 80% to 85% or at least 80%. In other embodiments, suitably transparent may mean that at least 80%, 85%, 90%, 95% or 98% of the visible light is capable of being transmitted through the substantially cured or cured composition. The visible light transmission of the substantially cured composition may be measured using suitable techniques, such as the spectrometer.

Certain embodiments relate to an intraocular lens comprising a polymer with an organosilicon compound and hydrolytically sensitive siloxane moiety and having one or more properties of an elastic modulus of 6 kPa or less; less than 20% of post-cure extractables. Other embodiments relate to an accommodating intraocular lens comprising a polymer with an organosilicon compound and hydrolytically sensitive siloxane moiety and having one or more properties of an elastic modulus of 6 kPa or less; less than 20% of post-cure extractables with at least 50% of the extractables having $M_n$ greater than about 30,000. Other embodiments relate to an accommodating intraocular lens comprising a polymer with an organosilicon compound and hydrolytically sensitive siloxane moiety and having one or more properties of an elastic modulus of 6 kPa or less; less than 20% of post-cure extractables with at least 50% of the extractables having $M_n$ greater than about 30,000 and a refractive index in range of about 1.4 to about 1.5.

Certain other embodiments relate to an accommodating intraocular lens comprising an organosilicon compound and hydrolytically sensitive siloxane moiety polymer and having one or more properties of an elastic modulus of 6 kPa or less, less than 20% of post-cure extractables, at least 50% of the extractables having $M_n$ greater than about 30,000, a refractive index in the range of about 1.4 to about 1.5 and a dioptric range of accommodation of 0.5D to 10D. Certain other embodiments relate to an accommodating intraocular lens comprising an organosilicon compound and hydrolytically sensitive siloxane moiety polymer and having one or more properties of an elastic modulus of 6 kPa or less, less than 20% of post-cure extractables, at least 50% of the extractables having $M_n$ greater than about 30,000, a refractive index in the range of about 1.4 to about 1.5 and a dioptric range of accommodation of 0D to 10D.

The present disclosure further relates to a kit comprising one or more of a) injectable composition comprising an organosilicon compound and a hydrolytically sensitive siloxane moiety and having a specific gravity greater than 0.95 b) an injection device and/or c) a valve device. The injection device may be prefilled with the injectable composition or the injectable composition may be available for refilling into the device at a later stage. The injection device may consist of a syringe and a cannula. The syringe and cannula may be designed to support manual injection of the composition into the capsular bag of an eye of a patient without undue force. The cannula may be designed to be compatible with a small capsulorrhexis of the capsular bag. The cannula may be capped with a protective sleeve.

The injectable composition is typically delivered using the injection device as described herein into the capsular bag of the eye of a warm blooded animal through a small aperture created with an incision or capsulorrhexis of the anterior capsular surface of the eye. Leakage of the injected composition from the capsular bag into the surroundings through the small incision or capsulorrhexis is undesirable. Thus the kit may further comprise a valve device which may be used to seal or plug or close or approximate the aperture on the capsular surface preventing leakage of the composition from the capsular bag of the eye. The valve may be an one-piece minicapsulorrhexis valve for example, as described in U.S. Pat. Nos. 7,001,426 and/or 6,358,279 or a similar device and may be used at one or more of the following phases: prior to filling, during filling and after filling of the capsular bag of the eye of a warm blooded animal to prevent, or substantially prevent, leakage of the composition.

The present disclosure is directed, at least in part, to compositions that have one or more of the following characteristics and/or advantages:
  the composition prior to cure has a viscosity range such that it is injectable;
  the injectable composition on visual inspection is colourless, substantially colourless or sufficiently colourless;
  the injectable composition is transparent, substantially transparent, suitably transparent or sufficiently transparent;
  the injectable composition is safe for use in situ in an eye of a warm blooded animal due at least in part to the moisture cure mechanism;
  the cured composition is safe for use in situ in an eye of a warm blooded animal due at least in part to the moisture cure mechanism
  the cured composition is transparent, substantially transparent, suitably transparent or sufficiently transparent;
  the cured composition is sufficiently able to change shape due at least in part to the modulus of the cured composition;
  the cured composition has a refractive index that is close, or suitably close to the refractive index of the crystalline lens of the eye of the warm blooded animal;
  the cured composition is able to achieve a sufficient dioptric range of accommodation.

DETAILED DESCRIPTION

The present disclosure is described in further detail with reference to one or more embodiments. The examples and embodiments are provided by way of explanation and are not to be taken as limiting to the scope of the disclosure.

The term "comprise" and its derivatives (e.g., comprises, comprising) as used in this specification is to be taken to be inclusive of features to which it refers, and is not meant to exclude the presence of additional features unless otherwise stated or implied.

The features disclosed in this specification (including accompanying claims and abstract) may be replaced by alternative features serving the same, equivalent or similar purpose, unless expressly stated otherwise.

In the context of this specification, the terms "a" and "an" are used herein to refer to one or to more than one (i.e. to at least one) of the grammatical object of the article. By way of example, "an element" means one element or more than one element.

The subject headings used in the detailed description are included for the ease of reference of the reader and should not be used to limit the subject matter found throughout the disclosure or the claims. The subject headings should not be used in construing the scope of the claims or the claim limitations.

As used herein, the term "organosilicon compound" is understood to refer to compounds that contain silicon-carbon bonds in their molecules such as polydimethylsiloxanes.

As used herein, the term "hydrolytically sensitive siloxane moiety" is understood to refer to a siloxane or silyl substituent that, upon coming into contact with moisture, or water and/or an aqueous medium undergoes a reaction with the water molecule to liberate a small condensation product and leave a reactive silanol in its place.

As used herein, in certain embodiments, the term "curing" is understood to refer to the process, for example, crosslinking by which macromonomers are converted into a three dimensional higher molecular weight polymer that is a solid, semi-solid, gel or combinations thereof. In certain embodiments, the term "curing" is understood to refer to the crosslinking of the molecules in the injected composition to form a substantially continuous network that may be a solid, semi-solid, gel like or combinations thereof. In certain embodiments, the term "substantially cured" is understood to refer to the formation of a substantially continuous polymer network that may be a solid, semi-solid, gel-like or a combination thereof.

As used herein, the term "in situ" is understood to refer to the phenomenon, processes and/or results occurring in place.

As used herein, the term "capsule" is understood to refer to the capsular bag of the eye of a warm blooded animal or an artificial situation simulating the capsular bag of the eye such as capsular moulds in a laboratory situation.

As used herein, the term "aqueous medium" is understood to refer to water based solutions, water, moisture or combinations thereof.

As used herein, the term "injectable" is understood to refer to the process or procedure by which the composition can be delivered or introduced or transported or pumped by force through a tube or duct or passage or canal or cavity or channel to the site of delivery i.e. the capsule.

As used herein, the term "injectable composition" is understood to refer to a composition that is capable of being injected. Typically, the injectable composition refers to a composition that is not cured or substantially not cured. In certain applications, the injectable composition may be partially cured prior to being injected and/or placed in situ.

As used herein, the term "cannula" is understood to refer to devices that can be used to inject or deliver or introduce the composition to the required site i.e. the capsule and includes cannula, cannula like devices, needles, needle-like devices, tubes, tubing, catheters and all devices with a bore used for injection or delivery of the composition to the site.

As used herein, the term "syringe" is understood to refer to a device or instrument that is used to hold and transport the composition to the site and includes syringe, syringe like devices, cylinders, cartridges, pumps and all devices used for injection of the composition to the site.

As used herein, the term "extractables" is understood to refer to the composition and/or quantity of material removed into solution from a cured macromonomer through the direct immersion of the cured polymer in a solvent that solubilizes suitable macromonomers, or higher oligomers thereof.

As used herein, the term "modulus" is understood to refer to the compressive or shear force, measured in kPa, required to deform a cured macromonomer.

As used herein, the term "mole fraction of the end groups" is understood to refer to the ratio, or percentage, of polymer end groups that possess a hydrolysable and cross linkable moiety as compared with the total number of polymer end groups available for functionalization. The "mole fraction of functionalized end groups" may be determined by methods using Nuclear Magnetic Resonance (NMR) assessment and/or Gel Permeation Chromatography (GPC) assessment in order to determine the molecular weight of the product. This may be followed by using either quantitative NMR to determine the percentage of polymer end groups functionalized and/or the titration of the polymer using a wet chemistry method to quantify the hydrolysis products generated in order to calculate the stoichiometry of the hydrolysis product to the number of available end groups on the polymer (based on its molecular weight as determined by NMR and/or GPC).

The moisture curing capability is introduced to the macromonomer i.e. the organosilicon compound though the introduction of either or a mixture of, silyl esters group as outlined in Structure A, and silyl ether groups as described in Structure B.

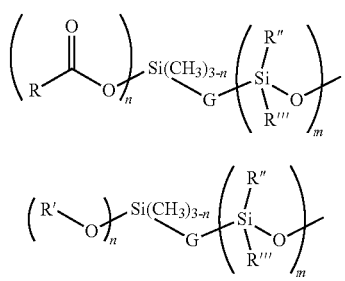

Structure A

Structure B

Where; $R=R'=CH_3$, $CH_3CH_2$—, $CH_3CH_2CH_2$—, $(CH_3)_2CH$—, and higher branched and straight aliphatic chains, aromatic and substituted aromatic, both of which may also contain heteroatoms such as N, S and halogens.

$R''=CH_3$ or Ph or $CH_3CH_2$—, $CH_3CH_2CH_2$—, $(CH_3)_2CH$—, and higher branched and straight aliphatic chains, aromatic and substituted aromatic, both of which may also contain heteroatoms such as N, S and halogens $R'''=CH_3$ or Ph or $CH_3CH_2$—, $CH_3CH_2CH_2$—, $(CH_3)_2CH$—, and higher branched and straight aliphatic chains, aromatic and substituted aromatic, both of which may also contain heteroatoms such as N, S and halogens n=1, 2 or 3

G=Group attaching functionality to polymer, usually —(—O—)—, or —(—CH2CH2-)—, resulting from the functionality being introduced to the polymer through condensation, hydrosilation, or nucleophilic substitution reactions.

m>1, and represents the polysiloxane component of the linear or branched copolymer that constitutes the macromonomer (organosilicon compound).

Both of these classes of siloxane are hydrolytically sensitive—reacting with water, moisture and/or an aqueous medium to release the ester or alcohol hydrolysis product, and in the process, generating a silanol functionality. The silanol group may undergo further condensation reactions with other silanols, as well as with the precursor silyl ester and silyl ether groups. The silanol condensation reactions between the polymer macromonomers may result in the crosslinking of the macromonomers into a continuous covalent network. For the purpose of ensuring a high degree of incorporation of the macromonomer into the cured composition siloxane functionalities bearing multiple functionality at the end of the polymer chains may be included. Scheme 1 provides an example of a triethoxy-end group employed for a linear siloxane resulting in hexafunctionality with respect to opportunities for incorporation into matrix Similarly Scheme 2 provides the example of the incorporation of a diacetoxymethyl end group on a linear siloxane resulting in a tetrafunctional precursor macromonomer.

Scheme 1

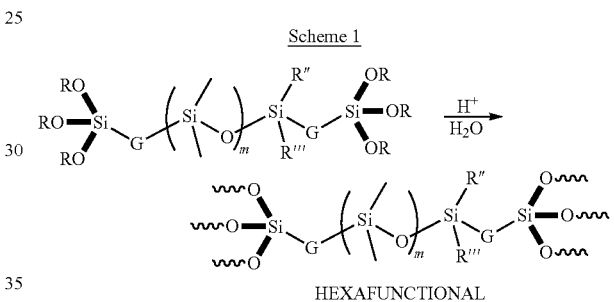

HEXAFUNCTIONAL

Scheme 2

TETRAFUNCTIONAL

The benefits may be magnified with the use of a branched macromonomer as in Scheme 3.

Scheme 3

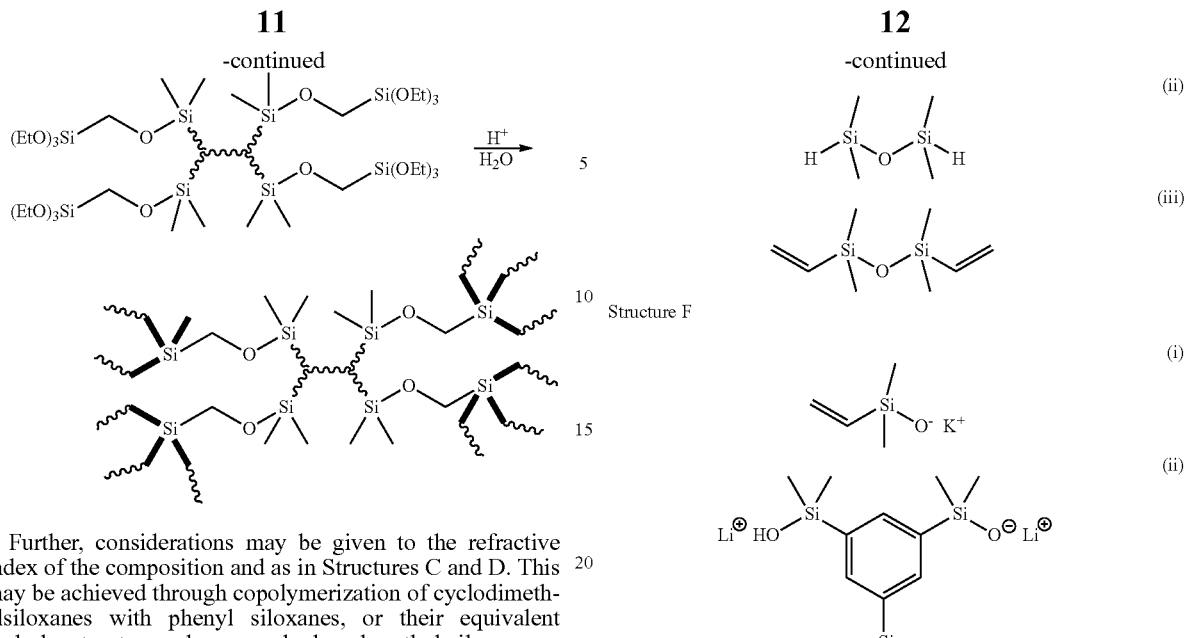

Further, considerations may be given to the refractive index of the composition and as in Structures C and D. This may be achieved through copolymerization of cyclodimethylsiloxanes with phenyl siloxanes, or their equivalent hydrolozates to produce a polyphenyl-methyl-siloxane or polydiphenylsiloxane copolymer as depicted in structures C and D.

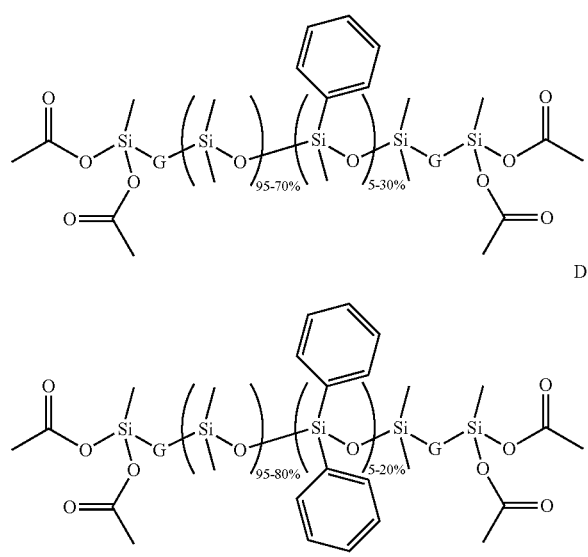

Also, the desired molecular weight of the injectable composition may be achieved through the moderation of the end group (such as those depicted in Structures E(i) to (iii)) concentration during cationic ring opening polymerisation (ROP), using such catalysts as triflic acid, sulphuric acid, or Amberlyst (Dow), or may be controlled in an anionically initiated ROP through the ratio of monomer to "endcapper" (such as those depicted in Structure E(i) to (iii) or an initiatior (such as Structure F(i) and (ii)).

Structure E

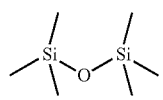

(i)

Structure F

Also, branching within the composition may be introduced by a number of ways. For example, a symmetrical difunctional linear precursor may be used in a hydrosilation reaction with a polyfunctional core (Scheme 4a and 4b) with either vinyl end groups or hydride end groups on the polymer chains.

Macromonomers (organosilicon compounds) with a range of desired architectures may be generated by altering: the molecular weight of the precursor polymer and/or the ratio of end-group functionalised polymer to core and/or the numerical functionality of the core (Tris(dimethyvinylsiloxy) phenylsilane (TDVPS)—3 arm core, (Tetrakis-(dimethylvinylsiloxy)-silane) (TDVS)—4 arm, 1,3,5,7,9,11-Hexavinyl-5,9-dibutoxytricyclo[5.5.1.1(3,11)] hexasiloxane—6 arm, etc). The residual functionalities remaining on the macromolecular oligomeric structure, which may be capable of undergoing hydrosilation chemistry (i.e. a Si—H or Si-Vinyl), are subsequently reacted in the presence of a catalyst to introduce the hydrolisable and condensable siloxane moiety. To deliver the functionality of the desired starting polymer, hydrosilation reaction using dimethylethoxyvinylsilane, methyldiethoxyvinylsilane, triethoxyvinylsilane, diethoxymethylvinylsilane, vinyldiacetoxymethylsilane, vinyldimethylacetoxysilane may be used. Correspondingly for vinyl terminated polymer chains; diethoxymethylsilane, diacetoxymethylsilane, dimethylethoxysilane, dimethylacetoxysilane, triethoxysilane may be used. Catalysts such as chloroplatinic acid, Karstedt's catalyst, palladium acetate and platinum oxide may be employed.

Scheme 4(a)

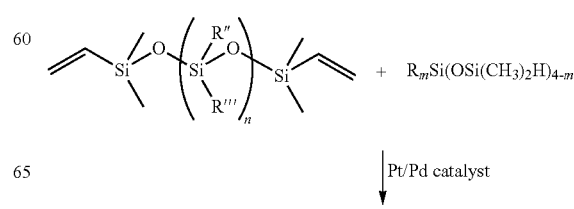

-continued

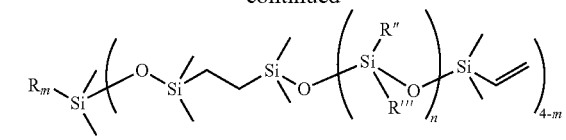

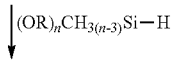

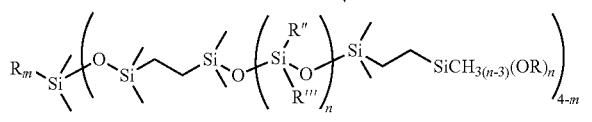

-continued

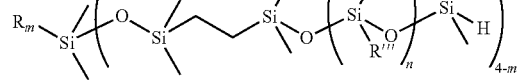

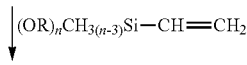

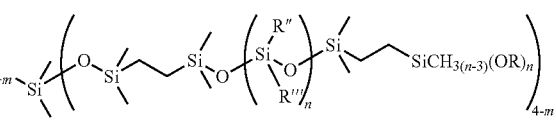

Initiators as the type described in figure F (ii) may have the advantage of producing narrow polydispersity functionalised macromers—relative to the oligomeric type structures obtained by one pot hydrosilations as disclosed in Scheme 4. Examples of the use of such initiators are included in Scheme 5 in order to demonstrate the applicability of such architectures.

Scheme 4(b)

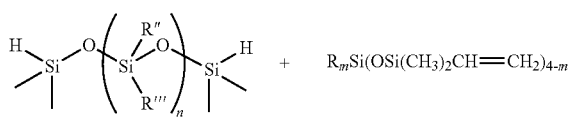

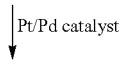

Scheme 5

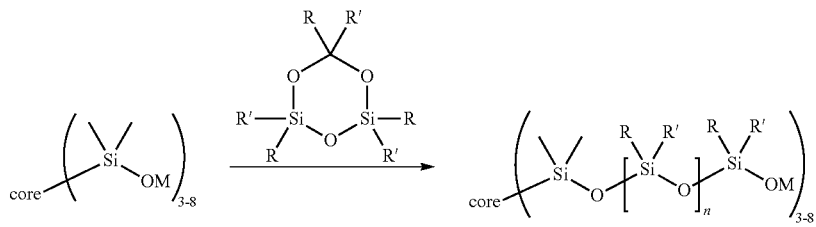

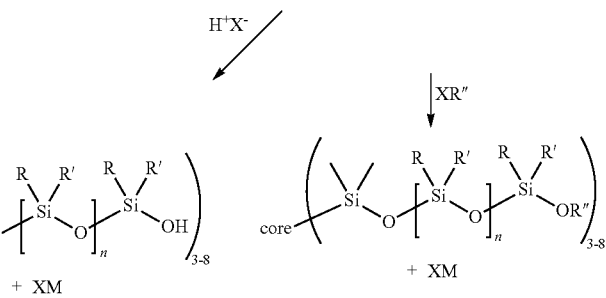

M = Li, Na, K
R = Alk, Ar, vinyl, H
R' = Alk, Ar
X = Cl, Br, LG
R" =

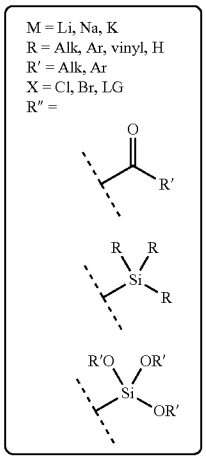

The following examples illustrate the process of preparation of functionalization of the linear and/or branched macromonomer (organosilicon compound). It should be understood that what is illustrated is set forth only for the purposes of example and should not be taken as a limitation on the scope of the present disclosure.

EXAMPLE 1

Synthesis of Si—H Terminated 3.1:1 Branched PDMS Macromonomer

A stock solution of Tris (dimethyvinylsiloxy) phenylsilane stock solution (TDVPS) was prepared by dissolving TDVPS (1.603 g) in 95.625 g of dry toluene (1.649%). Also diluted Karstedt's catalyst (Platinum (0)-1,3-divinyl-1,1,3,3-tetramethyldisiloxane catalyst) was prepared by dissolving 1 mL of Karstedt's catalyst (2% Pt in xylene) in dry toluene (100 mL).

Thereafter, DMS-H31 (Gelest) (30.928 g, 1.2315×10-3 mol), anhydrous toluene (80 mL), TDVPS stock solution (9.848 g, 3.973×10-4 mol) to give 3.1:1 branched PDMS macromonomer and Karstedt's catalyst solution (1 mL), were introduced to a three neck flask containing a magnetic stirrer, connected to a condenser under nitrogen and the mixture was stirred and heated for 2 h at 70° C. The completion of the reaction was monitored by 1H NMR. The disappearance of vinyl signals at around 6 ppm confirmed the completion of the reaction, and the reaction flask was removed from the condenser. Anhydrous toluene (30 mL) was added to dilute the mixture, followed by activated carbon, and the mixture stirred overnight at room temperature. A small amount of the reaction mix was withdrawn for characterisation. 1HNMR (CDCl3, ppm) δ=0.074 (Si—(CH$_3$)$_2$, b), 0.18 ((CH$_3$)$_2$—Si—H, d), 0.45 (—CH$_2$—CH$_2$—, m), 4.706 ((CH$_3$)$_2$—Si—H, h), 7.25-7.7 (Aromatic H, m), GPC (THF): Mn: 46252, Mw: 94463, Mw/Mn: 2.04, viscosity 13.34 Pa·s.

EXAMPLE 2

Synthesis of Si—H Terminated PDMS Macromonomer: 3.2:1

The procedure was as outlined previously for 3.1:1 DMS-H31/TDVPS MM except that 47.66 g, 1.8978×10-3 mol DMS-H31 and TDVPS (1.603 g) were used. 1H NMR (CDCl3, ppm) δ=0.068 (Si—CH3, b), 0.184 (CH3-Si—H, d), 0.418 (—CH2-CH2-, b), 4.70 (CH3-Si—H, h), 7.25-7.7 (Aromatic H, m), GPC (THF): Mn: 45127, Mw: 91101, Mw/Mn: 2.02, viscosity 9.798 Pa·s Examples 1 and 2 were repeated with a range of DMS-H31/TDMS ratios, with DMS-H25 (Gelest) and with various catalysts, to synthesise macromonomers as outlined in Tables 1 and 2.

TABLE 1

Synthesis of macromonomers in varying ratios

| Polymer | n(Si—H PDMS H31) | n(trisvinyl core) | Ratio | Catalyst | GPC: THF* & polysyrene standards Mn | Mw | Mw/Mn | Viscosity (Pa · s) |
|---|---|---|---|---|---|---|---|---|
| | Starting material H31 | | | | 25113 | 37732 | 1.50 | 1.30 |
| 1 | 3.1 | 1 | 3.1:1 | Karstedt | 46252 | 94463 | 2.04 | 13.34 |
| 2 | 3.2 | 1 | 3.2:1 | Karstedt | 47107 | 91243 | 1.94 | 9.80 |
| 3 | 3.3 | 1 | 3.3:1 | Karstedt | 44178 | 87689 | 1.98 | 9.11 |
| 4 | 3.4 | 1 | 3.4:1 | Karstedt | 43441 | 86567 | 1.99 | 8.81 |
| 5 | 3.5 | 1 | 3.5:1 | Karstedt | 42653 | 84238 | 1.97 | 7.92 |
| 6 | 3.6 | 1 | 3.6:1 | Karstedt | 42000 | 83694 | 1.99 | 7.45 |

*THF—Tetrahydrofuran

TABLE 2

Synthesis of macromonomers in varying ratios

| Si—H terminated macromonomer | n(Si—H PDMS H31) | n(trisvinyl core) | Ratio | Catalyst | GPC: THF* & polysyrene standards Mn | Mw | Mw/Mn | Viscosity (Pa · s) |
|---|---|---|---|---|---|---|---|---|
| | Starting material H31 | | | | 26160 | 40359 | 1.5 | 1.30 |
| 1 | 3.0 | 1 | 3:1 | PtO2 | 47566 | 127972 | 2.69 | 16.77 |
| 2 | 4.0 | 1 | 4:1 | PtO2 | 38568 | 92920 | 2.41 | 7.02 |
| | Starting material precipitated H31 | | | | 26079 | 39281 | 1.51 | 1.75 |
| 3 | 3.0 | 1 | 3:1 | PtO2 | 52291 | 113409 | 2.17 | 30.00 |
| | Starting material H25 | | | | 17200 | | | |
| 4 | 3.0 | 1 | 3:1 | PtO2 | 20511 | 46209 | 2.25 | 1.77 |
| 5 | 4.0 | 1 | 4:1 | PtO2 | 20122 | 45621 | 2.27 | 1.53 |
| | Starting material precipitated H25 | | | | 29255 | 42451 | 1.45 | 0.75 |
| 6 | 3.0 | 1 | 3:1 | PtO2 | 22736 | 51610 | 2.27 | 1.89 |

*THF—Tetrahydrofuran

EXAMPLE 3

Synthesis of α,ω-divinyl Terminated Mid-index methylphenylsiloxy-PDMS Copolymer (Vt-PDMS-co-PPMS) Via Cationic Polymerisation Octamethylcyclotetrasiloxane (40.5 g), 1,3,5,7-phenylmethyl-cyclotetrasiloxane (mixture of D3Ph, D4Ph) (35.0 g), divinyltetramethyldisiloxane (1.2 mL) and trifluoromethanesulfonic acid (40 uL) were stirred at room temperature for 24 hours. The reaction was diluted with pentane (50 mL) and sodium carbonate (3 g) was added and stirred for a further 24 hours. Thereafter, sodium carbonate salt was filtered and solvent removed under vacuum. The resultant polymer was purified by washing with 9% toluene in methanol, followed by 9% pentane in methanol. The majority of solvent was removed under low vacuum and residue solvent removed under high vacuum. 1Hnmr (CDCl3, ppm)=−0.3-0.15 ppm (Si—(CH3)2, b), 0.16 ppm —CH2=CH2-Si—(CH3)2, s), 0.2-0.42 ppm (—CH3-Si-Ph, b), 5.5-6.5 ppm (—CH2=CH2 m), 7.2-7.6 ppm (Aromatic protons, two b). % mole vinyl content: 1.76. GPC (toluene): Mn: 47496, Mw: 13547, Mw/Mn: 1.8.

EXAMPLE 4

Synthesis of α,ω-divinyl Terminated Mid-index methylphenylsiloxy-PDMS Copolymer (V-PDMS-co-PMPS-V) by Anionic Polymerisation D4 (150.50 g) and D3,4Ph (48.98 g) and a magnetic stirrer were introduced into a 500 mL 3 neck flask. The flask was connected to a condenser and the top of the condenser connected to a N2 line. The flask was sealed with a stopper and a septum. The reaction flask was flushed with N2 for 30 mins. Then 40 mL of dry THF was added to dissolve the monomers and the flask was immerged into a 70 degrees oil bath for 20-30 mins.

Potassium dimethylvinylsilane was weighed in 100 mL RBF in the dry box and the flask sealed with a septum. 40 mL of dry THF was added to dissolve silanolate which was then added to the monomer solution using syringes and then another 40 mL of dry THF was added to rinse the silanolate flask to ensure that silanolate initiator was transferred to the reaction flask. After the silanolate solution and the washing were added, the starting time for the reaction was recorded and left stirring at 70 degrees for 90 mins and then the reaction removed from the oil bath. A pale yellow and viscous mixture was observed. Then chlorodimethylvinylsilane (1.4 mL) was added using a syringe. With the addition of chlorosilane, the yellow colour disappeared and the reaction turned slightly hazy due to the formation of potassium chloride salt. The reaction was left to stir at room temperature for 3 h.

Thereafter, THF and excess chlorosilane were pumped out resulting in a hazy and viscous polymer was obtained. Methanol 8×250 mL was added and stirred for few mins. Then the reaction mix was let to stand for some time to ensure that the polymer settled to the bottom of the flask and methanol removed by decantation. Residue methanol was removed using vacuum pump resulting in a transparent and viscous material.

$^1$H NMR (CDCl3, ppm) δ=0.074 (Si—(CH3)3, b), 0.158 (—(CH3)2-Si—CH=CH2), s), 0.288 (CH3-Si-Ph), 5.69-6.14 (—CH=CH2), 7-7.5 (Aromatic H, b), RI=1.431 and density=1.08467 g/mL. GPC(Toluene): Mn: 15,218, Mw: 33,392, Mw/Mn: 2.19

EXAMPLE 5

Synthesis of α,ω-divinyl Terminated Mid-index methylphenylsiloxy-PDMS Copolymer (Vt-PDMS-co-PMPS) by Equilibrium Anionic ROP Octamethylcyclotetrasiloxane, (113.6 g), 1,3,5,7-phenylmethyl-cyclotetrasiloxane (mixture of D3, D4Ph,Me) (37.1 g) and divinyltetramethyldisiloxane (2 g or 2.472 mL) were introduced into a 500 mL three neck-flask. Dry THF (100 mL) and KOH pellets (2.3 g) were added and reaction heated at 70° C. under N2 for 24 h. After cooling, the reaction was diluted with hexane (100 mL) and transferred to a separating funnel. Milli-Q water (100 mL) was added and the mixture was shaken. Two layers formed. The mixture in the separating funnel was neutralised with a few mL of HCl (5M). The organic layer was dried with magnesium sulphate (6 g). The magnesium salt was then filtered and the solvent removed under high vacuum. The product was washed with methanol and residue methanol removed using a rotary evaporator followed by residual solvent removed under high vacuum. 1HNMR (CDCl3, ppm)=−0.3-0.15 ppm (Si—(CH3)2, b), 0.16 ppm-CH2=CH2-Si—(CH3)2, s), 0.2-0.42 ppm (—CH3-Si—Ph, b), 5.5-6.5 ppm (—CH2=CH2 m), 7.2-7.6 ppm (Aromatic protons, two b). % mole vinyl content: 1.07. GPC (toluene): Mn: 9,940, Mw: 20,203, Mw/Mn: 2.03. RI: 1.438; Viscosity: 2.752 Pa·s

EXAMPLE 6

Synthesis of Trimethoxy Terminated 3.6:1 TDVPS/DMS-H31 Branched Macromonomer

Dilution of Karstedt's catalyst (Platinum (0)-1,3-divinyl-1,1,3,3-tetramethyldisiloxane catalyst): Karstedt's catalyst 2% Pt in xylene (1 mL) was dissolved in dry toluene (100 mL).

Si—H terminated macromonomer (25.77 g) made as in Example 1, was introduced to a flask with a magnetic stirrer, and connected to a condenser under nitrogen. Anhydrous toluene (130 mL), 0.371 mL of trimethoxy vinyl silane and 1 mL of 0.02% Karstedt's catalyst solution were introduced into the reaction flask and the reaction mix stirred overnight at 70° C. under nitrogen atmosphere. The completion of the reaction was monitored by $^1$H NMR. The disappearance of Si—H peaks at 4.7 ppm confirmed the completion of the reaction. Then anhydrous toluene (20 mL) was added to dilute the reaction mixture, followed by activated carbon and the mixture stirred overnight at room temperature. Thereafter, the carbon was filtered and toluene removed by rotary evaporator. The residual solvent was removed using a high vacuum pump to yield the desired functionalised macromonomer. $^1$H NMR (CDCl3, ppm) δ=0.0727 (Si—CH3, b), 0.4337 (—CH2-CH2-, b from Si—H staring macromonomer), 0.572 (—CH2-CH2-, b), 3.574 (—OCH3, s), 7.26-7.31 (Aromatic H, b).

EXAMPLE 7

Synthesis of Acetoxy Terminated Branched Macromonomer 28.0 g of Si—H terminated macromonomer made as in Example 1 was introduced to a flask with a magnetic stirrer and connected to a condenser under nitrogen. Anhydrous toluene (40 mL), glacial acetic acid (0.16 mL) and a spatula tip of palladium acetate were introduced into the reaction flask and the reaction mixture stirred overnight at 70° C. under nitrogen. The completion of the reaction was monitored by $^1$H NMR. The disappearance Si—H peaks at 4.7 ppm confirmed the completion of the reaction. Anhydrous toluene (20 mL) was added to dilute the reaction mixture followed by activated carbon and the mix stirred overnight at room temperature. The carbon was then filtered and the toluene removed by rotary evaporator. The residual solvent was removed using high vacuum pump. $^1$H NMR (CDCl3, ppm) δ=0.068 (Si—CH3, b), 0.284 (CH3)2Si—O—CO—CH3, s), 0.43 (—CH2-CH2-, b), 2.058 (—Si—O—CO—CH3, s), 7.26-7.31 (Aromatic H, b)

EXAMPLE 8

Synthesis of Methoxy-terminated Linear PDMS Via Hydrosilation 5 g of DMS-H31 (Gelest) (1.99×10-4 mol) and 2 g (1.35×10-2 mol) of vinyl trimethoxy silane (excess) were placed in a 100 mL round bottom flask with a magnetic stirrer. Toluene (20 mL) was added to dissolve the reactants followed by platinum oxide (PtO2) catalyst (50 mg) and the mixture stirred at 70° C. for 2 hours. The reaction was monitored by $^1$H NMR. The disappearance of the Si—H bond at δ=4.70 ppm confirmed the completion of the hydrosilation reaction. After purification by vacuum distillation (Kugelrohr), the product was isolated as colourless liquid, which was characterized by 1H NMR spectroscopy. δppm, (0.067 Si—CH3, b), 0.571(—CH2-CH2-, b), (3.573-OCH3 s)

EXAMPLE 9

Synthesis of Ethoxy-terminated Linear PDMS Via Condensation 13 g (7.22×10$^{-4}$ mol) of DMS-S27 (Gelest) was mixed with 20 mL (1.3×10$^{-1}$ mol) of Methyl triethoxy silane (MeTEOS) and the reaction mixture was connected to a Dean Stark apparatus. The reaction mixture was heated from ambient temperature to boiling over 15 min, and then refluxed for 90 min. Excess MeTEOS was removed via Dean Stark apparatus. NMR confirmed that the reaction had proceeded successfully, also indicating the presence of a small amount of residual MeTEOS—which was then removed by Kugelrohr apparatus. The product was isolated as colourless viscous oil that was characterized by $^1$H NMR (0.067 Si—CH3, b), 3.515-OCH3 s).

EXAMPLE 10

Synthesis of Ethoxy-terminated Linear PDMS Via Hydrosilylation 5 g of DMS-H31 (1.99×10$^{-4}$ mol) and 2 mL (9.49×10$^{-3}$ mol (excess) of Diethoxy (methyl)vinylsilane were placed in a 100 mL round bottom flask with a magnetic stirrer. Toluene (20 mL) was added to dissolve the reactants followed by platinum oxide (PtO$_2$) catalyst (50 mg) and the mixture stirred at 70° C. for 2 hours. The reaction progress was followed by $^1$H NMR. The disappearance of the Si—H bond at δ=4.70 ppm confirmed the completion of the hydrosilation reaction. Reaction mixture was filtered to remove the platinum catalyst. After purification by distillation, removal of excess diacetoxymethylvinylsilane was achieved through heating under vacuum (Kugelrohr), and the product isolated as a colourless oil, which was characterized by $^1$H NMR (0.067 Si—CH$_3$, b), 0.571(—CH$_2$—CH$_2$-b), 3.83 (—CH$_2$-) q), 1.23 (—CH$_3$, t).

EXAMPLE 11

Synthesis of Ethoxy-terminated Linear PDMS Via Condensation 6.26 g of DMS-S35 (Gelest) was mixed with 20 mL of Tetraethyl orthosilicate (TEOS) and the reaction mixture connected to a Dean Stark apparatus. The reaction mixture was heated from ambient temperature to boiling overly min and refluxed for 90 min. Excess MeTEOS was removed via Dean Stark apparatus. NMR confirmed that the reaction proceeded to completion, but indicated the presence of trace residues of MeTEOS, which were removed by heating on a Kugelrohr under high vacuum. The product was isolated as colourless oil. (0.072 Si—CH$_3$, b), (1.245 CH$_2$—C$\underline{H}_3$, t,) (3.863 C$\underline{H}_2$—CH$_3$, q).

EXAMPLE 12

Synthesis of Acetoxy Terminated Linear PDMS Using Palladium Acetate

DMS-H31 (30 g, 1.147×10-3 mol) was weighed in a 250 mL three neck flask containing a magnetic stirrer. The reaction flask was connected to a condenser with a nitrogen gas inlet and purged with a positive pressure of nitrogen gas. Anhydrous toluene (50 mL), glacial acetic acid (0.05 mL) and a small spatula tip of palladium acetate was introduced to the reaction and stirred overnight at 70° C. The colour of the reaction mixture turned dark brown as the reaction progressed. The progress of the reaction was monitored by $^1$H NMR. The disappearance of Si—H peaks at 4.7 ppm confirmed the completion of the reaction, and activated carbon was added, and the reaction mixture stirred overnight at room temperature. Thereafter, the carbon was filtered and the toluene removed by rotary evaporator. The residue solvent was removed using high vacuum pump to obtain a transparent polymer. 1HNMR (CDCl3, ppm) δ=0.0701 (Si—CH3, b), 0.287 (CH3)2Si—O—CO—CH3, s), 2.0589 (—Si—O—CO—CH3, s).

EXAMPLE 13

Synthesis of Hydroxyl Terminated PDMS-co-PMPS

Octamethylcyclotetrasiloxane, (37.754 g) and Phenylmethyl-cyclosiloxanes (mixture of D3Ph,Me, D4Ph,Me) (12.264) were placed into a flask connected to a condenser under nitrogen. Dry THF (50 mL), and KOH (60 mg) were added. The reaction mixture was heated at 70° C. with stirring for 24 h. Milli-Q water (0.5 mL) was added followed by the removal of THF under vacuum. The reaction mixture was diluted by adding hexane (100 mL) and transferred to a separating funnel. Milli-Q water (100 mL) was added and the mixture shaken. Two layers formed. The reaction mixture was neutralised by adding 0.1M HCl until the pH of the aqueous layer was 7. The aqueous was discarded, and the organic layer washed with Milli-Q water (4×100 mL), transferred to a conical flask, added magnesium sulphate (3 g) and the mixture stirred at room temperature to dry the product. The product was washed with methanol (100 mL×3), with residue methanol removed using vacuum. 1Hnmr (CDCl3, ppm)=−0.2-0.18 (Si—(CH3), b), 0.2-0.45 (CH3)-Si-Ph), (7.25-7.7 (Aromatic H, m). GPC: Mn: 18160, Mw: 47579, Mw/Mn: 2.62. Viscosity: 2.752 Pa·s. RI: 1.438 and density: 1.096 g/mL

EXAMPLE 14

Diacetoxy Terminated Linear Polydimethyl-co-polyphenylmethyl Siloxane Copolymer Silanol terminated PDMS-co-PPMS was diluted in anhydrous tetrahydrofuran and added dropwise to a large excess of methyltriacetoxysilane that was in a liquid state due to the addition of a small amount of tetrahydrofuran. The mixture was allowed to stir for two days at room temperature.

The product was mixed with anhydrous acetonitrile which precipitated the siloxane (The excess methyltriacetoxy silane remained solubilised in the co-solvent layer). Upon separation the solvent was removed by vacuum. NMR (CDCl3,ppm)=0.0760 (Si—CH3, b), 0.318 (Ph-Si—CH3, b), 0.506 ((AcO)2-Si—CH3, s), 2.099 (CH3-Si—(OOCCH3)2, s), 7.25-7.7 (Aromatic H, m). Viscosity 5.63 Pa·s.

EXAMPLE 15

Preparation of Diethoxy Functionalised 3.1:1 Branched PDMS Macromonomer

Si—H terminated macromer (25.77 g) made as in Example 1 was dissolved in 160 mL of dry toluene, introduced to a flask with a magnetic stirrer and connected to a condenser under nitrogen. Diethoxy methylvinylsilane (0.47 mL) and 1 mL of Karstetd's catalyst solution were introduced to the reaction flask and the mix stirred overnight at 70° C. under nitrogen atmosphere. The completion of the reaction was monitored by 1H NMR. The disappearance Si—H peaks at 4.7 ppm confirmed the completion of the reaction. Then anhydrous toluene (20 mL) was added to dilute the reaction mixture followed by activated carbon and stirred overnight at room temperature. Then the carbon was filtered and toluene was removed by rotary evaporator. The residue solvent was removed using high vacuum pump and a viscous polymer was obtained. $^1$H NMR (CDCl3, ppm): 0.071 (Si—CH$_3$, b), 0.439 (—CH$_2$—CH$_2$—, b from Si—H staring macromolecule), 0.522 (—CH$_2$—CH$_2$—, b), 1.22 (Si—O—CH$_2$—CH$_3$, t), 3.78 (Si—O—CH$_2$—CH$_3$, q), 7.26-7.31 (Aromatic H, m).

EXAMPLE 16

Synthesis of Diacetoxy Functionalised Linear Polydimethylsiloxane-co-polydiphenylsiloxane Vinyl terminated (15-17% Diphenylsiloxane)-Dimethylsiloxane copolymer, PDV-1631, Gelest (52.12 g, 2.74×10-3 mol) and diacetoxy methyl silane (1.77 g, 1.1×10-3 mol) were placed in a round bottom flask with a magnetic stirrer in a glove box. Toluene (250 mL) was added to dissolve both compounds. 1 mL of Karstedt's catalyst, Pt(dvs), (2 mM solution in Toluene) was added and reaction mixture stirred at 70° C. overnight. The progress of the reaction was monitored by $^1$H NMR. The disappearance of the double bond from PDV-1631 confirmed that the reaction was completed. The bulk of solvent was removed via rotary evaporator, with the remaining toluene/excess of starting diacetoxy methyl silane removed under high vacuum. The product was obtained as a transparent and viscous liquid.

$^1$H NMR: δ=0.08 (CH3)2; 0.51 CH2; 2.103 COCH3; 7.31-7.58 Ph)

EXAMPLE 17

Synthesis of Diacetoxy Functionalised 3.6:1 Branched PDMS-co-PPMS Polymer

Methylphenyl-PDMS copolymer (46.09 g, 4.64×10-3 mol) and phenyltris(dimethylsiloxy)silane core (0.426 g, 1.288×10-3) (mol) were placed in a round bottom flask equipped with a magnetic stirrer in a glove box. Toluene (200 mL) was added to dissolve both compounds. Karstedt's catalyst, Pt(dvs), (1 mL of 2 mM solution in Toluene) was added and reaction mixture stirred at 70° C. for 4 hours. The progress of hydrosilylation was monitored by 1H NMR. The disappearance of Si—H bond from phenyltris(dimethylsiloxy)silane core indicated that the hydrosilylation was completed. Diacetoxymethylsilane (1.49 mL, 9.27×10-3 mol) was added and the reaction mix stirred overnight. Disappearance of the double bond shift confirmed the completion of the second hydrosilylation. The reaction mixture was further stirred overnight with activated carbon to remove Karstedt's catalyst, filtered and reduced by removing bulk of solvent under N2 via rotary evaporator. The remaining toluene/excess of starting diacetoxy methyl silane was removed under reduced pressure while the product was kept in the glove box. The product was obtained as a transparentand viscous liquid. Properties of branched acetoxy mid index polymer are: Viscosity—4.37 Pa·s.

EXAMPLE 18

Synthesis of Polymer Macromolecule with Reduced Polydispersity and Defined Architecture 1,3,5-Tris(dimethylsilanol)benzene (50 mg, 0.17 mmol) was dissolved in anhydrous THF (50 mL) in a dried RB flask under argon. 2.5 M BuLi solution in hexanes (0.20 mL, 0.50 mmol BuLi) was added and the solution stirred for 5 min. Separately, D$_3$ (10 g, 45 mmol) was weighed into a dried RB flask under argon and dissolved in anhydrous THF (30 mL). This monomer solution was added to the initiator solution and stirred at room temperature for 2 h. Chlorodimethylsilane (1 mL, 10 mmol) was added and the mixture stirred for 2 h before being concentrated in vacuo (20 mbar, 50° C.) to afford a milky oil. Anhydrous pentane (ca. 3×the volume of polymer) was added and the solution stirred under argon for 30 min. The insoluble lithium salts were filtered under argon and the filtrate concentrated in vacuo (20 mbar, 40° C.), followed by drying in vacuo (0.1 mbar, 120° C., 14 h), to afford the hydride-terminated star polymer as a colourless viscous oil.

EXAMPLE 19

Functionalisation of Reduced Polydispersity and Defined Architecture to Produce Diacetoxy Terminated Macromonomer 20.08 g of branched silanol terminated siloxane copolymer (Example 18. Silanol 100 kg/mol theoretical weight, PDI 1.3) was dissolved in 90 mL of anhydrous tetrahydrofuran and dried over magnesium sulphate. This mixture was then passed over activated neutral aluminium oxide followed by its dropwise addition into a vigorously stirring mixture of 16.54 mL of dimethyl diacetoxy silane and 0.206 mL of methyl triacetoxy silane. A further 90 mL of anhydrous tetrahydrofuran was added once the siloxane copolymer addition through the column was completed. Purification occurred by the addition of 300 mL of anhydrous acetonitrile which precipitated the product. A second precipitation was performed by the addition of 10 mL of anhydrous tetrahydrofuran and then 50 mL of anhydrous acetonitrile. Once separated the product was put under vacuum to remove trace levels of solvent.

$^1$HNMR (CDCl3,ppm)=−0.12-0.16 (Si(CH3)$_2$O, b) 0.16-0.37 (SiCH$_3$PhO, b), 0.367 (—Si(CH3)(Ar core), s), 0.518 ((AcO)2-Si—CH3, s), 2.107 (CH3-Si—(OOCCH3)$_2$, s), 7.25-7.7 (Aromatic H, b), 7.77 (3ArH core, s). Viscosity 1.252 Pa·s.

EXAMPLE 20

Synthesis of α,ω-divinyl Terminated Mid-index PDMS-co-PMPS Copolymer by Anionic Ring Opening Polymerisation-KOH D4 (113.6 g), D3,4 Ph mix cyclics (37.1 g), and divinyltetramethyldisiloxane (2.47 mL), dry THF (100 mL), KOH (0.25 g) were charged into a 500 mL round bottom flask equipped with a magnetic stirrer (dry box). The reaction flask was brought outside, connected to a Nitrogen gas and stirred at 70° C. for 20 hours. After the reaction mix temperature was brought ambient it was neutralised with Pentane (100 mL), milli-Q water (100 mL) and 5M HCl (0.5 mL) and stirred at room temperature for 30 mins. The reaction mix was then transferred into a separating funnel, mixed vigorously; bottom aqueous layer was discarded. Milli-Q water (100 mL) was added to the organic layer and the mix was shaken vigorously; the bottom aqueous layer was removed. The organic layer was washed with milli-Q water for three more times until the pH of the aqueous layer was around 5-6 (the pH of the mill-Q water). The organic layer was transferred into a conical flask and stirred with magnesium sulphate (7.47 g) overnight at RT. The suspension was transferred into an in house filtration unit and the salt was filtered off. The solvent was removed by rotary evaporator and vacuum pump overnight at room temperature to afford a clear polymer. The polymer was washed with methanol (70 mL) for 8 times until GPC showed no presence of the low molecular weight oligomers. The solvent was removed using rotary evaporator and vacuum pump at room temperature. A product was obtained was obtained that on a visual inspection was substantially colourless and substantially transparent.

$^1$H NMR (CDCl$_3$, ppm) δ=−0.05-0.2 (Si—(CH$_3$)$_2$), b), 0.1703 (CH$_2$=CH—Si—(CH$_3$)$_2$, s), 0.22-0.38 (—CH$_3$—Si-Ph, b), 5.6-6.2 (CH$_2$=CH—, m), 7.2-7.6 (Aromatic protons, two b). Mn: 10,232, Mw: 18,658, Mw/Mn: 1.8. RI: 1.438.

EXAMPLE 21

Synthesis of Diacetoxy Functionalised Macromonomer from α,ω-divinyl Terminated Mid-index PDMS-co-PMPS Copolymer α,ω-divinyl terminated mid-index PDMS-co-PMPS copolymer (50 g) and anhydrous toluene (250 mL) were introduced into a 500 mL one neck flask contained a magnetic stirrer and the reaction mix was mixed well. Phenyltris(dimethylsiloxy) silane (449 μL) and Karstedt's catalyst solution (1 mL) were added to the reaction mix. The reaction flask was stirred for 4 h at 70° C. The completion of the first reaction was monitored by $^1$H NMR; the disappearance of Si—H signals at around 4.7 ppm confirmed that the reaction was completed. Then diacetoxymethylsilane (1.3 mL) and Karstedt's catalyst (0.5 mL) were added to the reaction mix, stirred at 70° C. overnight. The reaction was monitored by NMR. The disappearance of the Si—H bond confirmed hydrosilylation. The reaction was stopped and activated carbon (4 g) was added and the reaction mix and stirred overnight at room temperature. The carbon was filtered off and toluene was removed by rotary evaporator and high vacuum pump (dry box). A product was obtained was obtained that on a visual inspection was substantially colourless and substantially transparent.

$^1$H NMR (CDCl$_3$, ppm) δ=−0.05-0.2 (Si—(CH$_3$)$_2$, b), 0.2-0.38 (—CH$_3$—Si-Ph, b), 0.43 (—CH$_2$—CH$_2$—, m, obtained from 1$^{st}$ hydrosilylation reaction), 0.51 and 0.939 ((—CH$_2$—CH$_2$—, m, obtained from 2$^{nd}$ hydrosilylation reaction), 0.502 ((CH$_3$—Si—(O—CO—CH$_3$)$_2$, s), (2.11 (—Si—(O—CO—CH$_3$)$_2$, s), 5.6-6.2 (CH$_2$=CH—, m, very low in intensity), (7.25-7.7 (Aromatic H, m), Mn: 14458; Mw: 55,135; Mw/Mn: 3.2; RI: 1.439; specific gravity: >1; viscosity: 3.93 Pa·s.

Example 22 below illustrates the process of preparation of the linear and/or branched macromonomer (organosilicon compound) that is partially functionalised, according to certain embodiments.

EXAMPLE 22

Synthesis of Diacetoxy Functionalised Macromonomer from α,ω-divinyl Terminated Mid-index PDMS-co-PMPS Copolymer (70% Diacetoxy, Core to Arm 3.85:1)

α,ω)-divinyl terminated mid-index PDMS-co-PMPS copolymer (Mn10,937, 42 g) and anhydrous toluene (250 mL) were introduced into a 1 L 3 neck flask that contained a magnetic stirrer and the reaction mix was mixed well at 70° C. Phenyltris (dimethylsiloxy) silane (350 μL) and Karstedt's catalyst solution (0.78 mL) were added to the reaction mix. The reaction flask was stirred for 5 h at 70° C. Then diacetoxymethylsilane (0.5 mL) and Karstedt's catalyst (0.4 mL) were added to the reaction mix, stirred at 70° C. overnight. The reaction was cooled down to ambient and activated carbon (7 g) was added. The reaction mix stirred overnight at room temperature. The carbon was filtered off and toluene was removed by rotary evaporator and high vacuum pump (dry box). A product was obtained was obtained that on a visual inspection was substantially colourless and substantially transparent. Mn: 19,967; Mw/Mn: 6.1: RI: 1.4403; Specific gravity: 1.02.

EXAMPLE 23

Synthesis of Diacetoxy Functionalised Macromonomer from α,ω-divinyl Terminated Mid-index PDMS-co-PMPS Copolymer (85% Diacetoxy, Core to Arm 3.85:1)

α,ω-divinyl terminated mid-index PDMS-co-PMPS copolymer (Mn10648, 42.65 g) and anhydrous toluene (250 mL) were introduced into a 1 L 3 neck flask contained a magnetic stirrer and the reaction mix was mixed well at 70°

C. Phenyltris (dimethylsiloxy) silane (365 μL) and Karstedt's catalyst solution (0.78 mL) were added to the reaction mix. The reaction flask was stirred for 5 h at 70° C. Then diacetoxymethylsilane (0.62 mL) and Karstedt's catalyst (0.40 mL) were added to the reaction mix, stirred at 70° C. overnight. The reaction was cooled down to ambient and activated carbon (7 g) was added. The reaction mix stirred overnight at room temperature. The carbon was filtered off and toluene was removed by rotary evaporator and high vacuum pump. A product was obtained was obtained that on a visual inspection was substantially colourless and substantially transparent. Mn: 21210; Mw: 116,613; Mw/Mn: 5.5; RI: 1.4423; Specific gravity: 1.02.

End-group variations: Using the approach outlined above various star polymers were prepared with different end-groups introduced by selection of the reactive species during the quenching step; e.g., acid chlorides were used to introduce mono-silyl ester end-groups; chlorosilanes were used to introduce hydride, vinyl and triethoxy end-groups, and ammonium chloride was used to introduce silanol groups. Characterisation of these polymers is provided below.

Silyl benzoate terminated star polymers with poly[(dimethyl siloxane)-ran-(methylphenyl siloxane)]-based were prepared via quenching with benzoyl chloride (270 equiv. relative to the initiator); $^1$H NMR (300 MHz, CDCl$_3$) $\delta_H$ −0.124-0.362 (m, Si(CH$_3$)$_2$ and SiCH$_3$Ph polymer backbone), 7.07-7.61 (m, ArH polymer backbone) 7.66-7.72 (m, ArH end-groups), 8.13-8.19 (m, ArH end-groups) ppm. GPC (relative to conventional linear polystyrene column calibration) M$_w$=72,000 Da; PDI=2.4.

Silyl hexanoate terminated star polymers with poly(dimethyl siloxane)-based aims were prepared via quenching with hexanoyl chloride (120 equiv. relative to the initiator); $^1$H NMR (300 MHz, CDCl$_3$) $\delta_H$ 0.076 (br s, Si(CH$_3$)$_2$ polymer backbone), 0.86-0.92 (m, CH$_2$CH$_3$ end-groups), 1.27-1.32 (m, CH$_2$CH$_2$CH$_3$ end-groups), 1.58-163 (m, CH$_2$CH$_2$CH$_2$ end-groups), 2.26-2.31 (m, O(CO)CH$_2$CH$_2$ end-groups), 7.78 (s, ArH core) ppm. GPC (relative to conventional linear polystyrene column calibration) M$_w$=100,000 Da; PDI=2.0.

Silyl acetate (i.e., acetoxy) terminated star polymers with poly(dimethyl siloxane)-based arms were prepared via quenching with acetyl chloride (120 equiv. relative to the initiator); $^1$H NMR (300 MHz, CDCl$_3$) $\delta_H$ 0.076 (br s, Si(CH$_3$)$_2$ polymer backbone), 2.05 (br s, O(CO)CH$_3$ end-groups), 7.77 (s, ArH core) ppm. GPC (relative to conventional linear polystyrene column calibration) M$_w$=88,000 Da; PDI=1.3.

Vinyl terminated star polymers with poly[(dimethyl siloxane)-ran-(methylphenyl siloxane)]-based arms were prepared via quenching with chloro(dimethyl)vinylsilane (30 equiv. relative to the initiator); $^1$H NMR (300 MHz, CDCl$_3$) $\delta_H$ −0.082-0.359 (m, Si(CH$_3$)$_2$ and SiCH$_3$Ph polymer backbone), 5.73 (dd, J=4.2 & 20 Hz, =CHH end-groups), 5.93 (dd, J=4.2 & 15 Hz, =CHH end-groups), 6.13 (dd, J=15 & 20 Hz, SiCHCH$_2$ end-groups), 7.09-7.61 (m, ArH polymer backbone) ppm. GPC (relative to conventional linear polystyrene column calibration) M$_w$=58,000 Da; PDI=1.5.

Hydride terminated star polymers with poly(dimethyl siloxane)-based arms were prepared via quenching with chlorodimethylsilane (60 equiv. relative to the initiator); $^1$H NMR (300 MHz, CDCl$_3$) $\delta_H$ 0.077 (br s, Si(CH$_3$)$_2$ polymer backbone), 0.19 (d, J=3 Hz, SiH(CH$_3$)$_2$ end-groups), 0.35 (s, ArSi(CH$_3$)$_2$ core), 4.71 (hept, J=3 Hz, SiH(CH$_3$)$_2$ end-groups), 7.77 (s, ArH core) ppm; M$_{n(NMR)}$=43,000 Da. GPC (relative to conventional linear polystyrene column calibration) M$_w$=31,000 Da; PDI=1.2.

Triethoxy siloxane terminated star polymers with poly (dimethyl siloxane)-based arms were prepared via quenching with chlorotriethoxysilane (60 equiv. relative to the initiator); $^1$H NMR (300 MHz, CDCl$_3$) $\delta_H$ 0.076 (br s, Si(CH$_3$)$_2$ polymer backbone), 1.21 (t, J=6.9 Hz, OCH$_2$CH$_3$ end-groups), 3.78-3.87 (m, OCH$_2$CH$_3$ end-groups), 7.78 (s, ArH core) ppm. GPC (relative to conventional linear polystyrene column calibration) M$_w$=46,000 Da; PDI=1.4.

Silanol terminated star polymers with poly[(dimethyl siloxane)-ran-(methylphenyl siloxane)]-based arms were prepared via quenching with ammonium chloride (60 equiv. relative to the initiator); $^1$H NMR (300 MHz, CDCl$_3$) $\delta_H$ −0.111-0.362 (m, Si(CH$_3$)$_2$ and SiCH$_3$Ph polymer backbone), 7.09-7.62 (m, ArH polymer backbone), 7.78 (s, ArH core) ppm. GPC (relative to conventional linear polystyrene column calibration) M$_w$ 33,600 Da; PDI=1.4.

Blending

In addition to above examples, blends with modifications in material properties may be prepared by mixing various percent concentrations (v/v) of diacetoxy terminated polydimethyl siloxane (DMS-D33) and branched macromonomer material (Diacetoxy terminated polydimethyl siloxane (Gelest)).

The composition of the above examples is loaded into a suitable injection device for injection into the capsular bag of the eye of a warm blooded animal or similar conditions such as for example, a capsular mould. The injection device may further comprise a syringe and a cannula. Once injected, the duration within which the composition may be substantially cured may range from minutes to days.

Determination of Extractables

The substantially cured polymer is removed from the capsular mould, blot dried and the initial weight recorded. Thereafter, the substantially cured polymer is soaked in pentane or suitable solvent for 3 days at room temperature. The extracted solvents are combined, centrifuged, filtered and dried to constant weight.

The percentage of extractable is calculated by dividing the extractable collected to the initial weight.

$$\% \text{ Extractable} = \frac{\text{extractable collected}}{\text{initial weight}} \times 100$$

Measurement of Modulus

For the determination of shear modulus, cured samples (at various cure times and temperatures) were investigated by TA instruments AR1000 rheometer. Experiments were conducted in oscillatory time sweep mode using a 20 mm steel plate. Samples applied to the peltier plate were exposed to a normal force of 0.2N. Upon reaching an equilibrium temperature of 37° C., operating parameters involved a frequency of 1.0 Hz and oscillatory stress of 125.0 Pa. This was employed to determine G' in units of kPa.

For the determination of compressive modulus, a custom built "micro-tensometer" that can measure mechanical properties of small and soft material samples, including compression and tensile modulus, toughness, creep and stress relaxation is used. Its two major components are a precision motorised linear actuator and a precision analytical balance, both controlled by dedicated application software. For the compression modulus testing of either explanted natural or refilled crystalline lenses or gel materials in disc or lens shape, the sample is loaded into the instrument using corresponding sample holders that provide full support at the underside of the sample. The sample is compressed from the top by the flat end face of a 2 mm diameter metal pin, which is attached to the linear actuator to be moved in a vertical direction. After loading the sample into the instrument, the pin moves downwards until it touches the sample surface. From the motor position, the actual sample thickness is calculated. The sample is then slowly compressed by 10% of its original thickness, while motor position and balance readings are acquired continuously. After reaching the preset compression, the motor moves back to the start position and after some recovery time, the measurement is repeated twice. Both readings are converted to obtain the stress/strain curves. Linear lines are fitted through the data points between 4% and 8% range. The averaged slope of these lines is the compression Young's modulus, Shear Modulus Testing of Oven Cured Macromonomers Samples were ejected into a 20 mm diameter polyoxymethylene mould to create a 600 mg sample measuring 2 mm in thickness. Moulds were cured at 35° C. for 24 hrs in a humid environment. This provided samples suitable for rheological modulus testing.

A sample of diacetoxy functionalised 3.6:1 branched PDMS-co-PPMS polymer from Example 17 was oven cured for 24 hours and the shear modulus measured on the AR1000 determined to be 0.599 kPa.

A sample of diacetoxy functionalised linear PDMS-co-PDPS polymer from Example 16 was oven cured and the shear modulus measured on the AR1000 determined to be 0.64 kPa.

Compressive Modulus Testing of In Vitro Membrane Cured Macromonomers

A 0.3 mL sample of diacetoxy functionalised 3.6:1 branched PDMS-co-PPMS polymer macromonomer from Example 17 was tied in medical grade collagen and immersed in 0.3 mL of Barany's solution at 37° C. for 7 days. The modulus of the cured material was measured on the microtensometer at 5.6 kPa.

A 0.3 mL sample of the diacetoxy functionalised reduced polydispersity of Example 19 was tied in medical grade collagen and immersed in 0.3 mL of Barany's solution at 37° C. for 7 days. The modulus of the cured material was measured by rheology. The shear modulus was 1.3 kPa; and the compressive modulus was 3.9 kPa.

A 0.3 mL sample of the diacetoxy functionalised macromonomer of Example 21 was tied in medical grade collagen and immersed in 0.3 mL of Barany's solution at 37° C. for 7 days. The modulus of the cured material was measured by rheology. The shear modulus was 1.7 kPa.

A 0.3 mL sample of the diacetoxy functionalised macromonomer of Example 22 was tied in medical grade collagen and immersed in 0.3 mL of BSS solution at 37° C. for 3 days. The modulus of the cured material was measured by rheology. The compressive modulus was 2.5 kPa.

A 0.3 mL sample of the diacetoxy functionalised macromonomer of Example 23 was tied in medical grade collagen and immersed in 0.3 mL of BSS solution at 37° C. for 3 days. The modulus of the cured material was measured by rheology. The compressive modulus was 5.5 kPa.

Shear Modulus Testing of Oven Cured Blends

A range of blend ratios, using various macromonomers reported in the preceding examples, were prepared and assessed.

A blend of 70% trimethoxy terminated 3.6:1 TDVPS/DMS-H31 branched macromonomer of the type from Example 6, and 30% DMS-D33 (Gelest) was oven cured for 24 hours and the shear modulus measured on the AR1000 determined to be 2.23 kPa.

A blend of 70% trimethoxy terminated 3.1:1 TDVPS/DMS-H31 branched macromonomer, and 30% DMS-D33 (Gelest) was oven cured for 24 hours and the shear modulus measured on the AR1000 determined to be 1.1604 kPa. Extractables 5.24%

A blend of 60% diethoxy terminated 3.1:1 TDVPS/DMS-H31 branched macromonomer, and 40% DMS-D33 (Gelest) was oven cured for 24 hours and the shear modulus measured on the AR1000 determined to be 0.262 kPa. Extractables 3.7%.

A blend of 70% diethoxy terminated 3.1:1 TDVPS/DMS-H31 branched macromonomer, and 30% DMS-D33 (Gelest) was oven cured for 24 hours and the shear modulus measured on the AR1000 determined to be 2.79 kPa. Extractables 5.11%.

Results of In Vivo Evaluation

A homogeneous blend (achieved by mixing 3 mL of DMS-D33 (Gelest) with 7 mL of diethoxy functionalised 3.6:1 branched PDMS macromonomer (Table 1) (30/70 v/v) was prepared, and transferred to a syringe.

1 female adult anaesthetised NZW rabbits underwent surgery in one eye wherein an anterior peripheral continuous mini-capsulorhexis of the crystalline lens capsule of approximately 1.0 mm diameter was performed, and the contents of the crystalline lens aspirated. After removal of the entire contents of the lens (nucleus and cortex), the capsular bag was refilled with a moderate quantity of viscoelastic to allow the insertion of a Mini-Capsular Valve (MCV; U.S. Pat. No. 6,358,279), to prevent leakage of the macromonomer during lens refilling from the bag into the anterior chamber. After the appropriate insertion of the MCV through the capsulorrhexis opening, the viscoelastic was emptied and the capsular bag refilled with the macromonomer blend. Using the slit-lamp illuminator mounted on the operation microscope, complete refilling was confirmed. On post-operative day 11, the animal was sacrificed and the formed intraocular lens removed (explanted) and subjected to mechanical testing, the results of which are presented below.

| Sample | Post operative days | Explanted lens - Modulus [kPa] | | |
|---|---|---|---|---|
| | | Repeat 1 | Repeat 2 | Repeat 3 |
| | 11 | 3.4 | 3.2 | 3.3 |

Additional examples of exemplary non-limiting embodiments are provided in numbered paragraphs below. Any reference to a numbered paragraph is reference to a paragraph within this section.

EXAMPLE A1

An injectable composition for forming an accommodating intraocular lens in situ in a capsule, comprising
an organosilicon compound and
a hydrolytically sensitive siloxane moiety
wherein the injectable composition has a specific gravity greater than about 0.95, a number average molecular weight ($M_n$) greater than about 5,000, a weight average molecular weight ($M_w$) greater than about 20,000 and is capable of being substantially cured in situ upon contact with moisture.

A2

The injectable composition of example A1, wherein the organosilicon compound comprises linear polysiloxane polymer chains, linear poly siloxane copolymer chains, branched polysiloxane polymer chains, or combinations thereof.

A3

The injectable composition of examples A1 or A2, wherein the injectable composition has a specific gravity in the range of about 0.96 to about 1.06.

A4

The injectable composition of example A1 or A2, wherein the injectable composition has a specific gravity in the range of about 0.99 to about 1.05.

A5

The injectable composition of example A1 or A2, wherein the injectable composition has a specific gravity in the range of 1 to 1.04.

A6

The injectable composition of one or more of examples A1 to A5, wherein the hydrolytically sensitive siloxane moiety comprises one or more of silane ether groups and/or one of more groups of silane ester groups.

A7

The injectable composition of one or more of examples A1 to A6, wherein the number average molecular weight ($M_n$) is in the range of about 5,000 to 150,000.

A8

The injectable composition of example A7, wherein the number average molecular weight ($M_n$) is in the range of about 5,000 to 100,000.

A9

The injectable composition of examples A7 or A8, wherein the wherein the number average molecular weight ($M_n$) is in the range of about 5,000 to 50,000.

A10

The injectable composition of one or more of examples A1 to A7, wherein the weight average molecular weight ($M_w$) is in the range of about 20,000 to 300,000.

A11

The injectable composition of example A10, wherein the weight average molecular weight ($M_w$) is in the range of about 20,000 to 200,000.

A12

The injectable composition of example A10 or A11, wherein the weight average molecular weight ($M_w$) is in the range of about 20,000 to 100,000.

A13

The injectable composition of one or more of examples A1 to A12, wherein the injectable composition has a viscosity greater than about 0.5 Pa·s.

A14

The injectable composition of example A13, wherein the injectable composition has a viscosity between 0.5 to 30 Pa·s.

A15

The injectable composition of one or more of examples A1 to A14, wherein the injectable composition has mole fractions of the end groups that possess a hydrolysable moiety and cross linkable moiety in the range of greater than about 20%.

A16

The injectable composition of example A15, wherein the injectable composition has mole fractions of the end groups that possess a hydrolysable moiety and cross linkable moiety in the range of about 20% to 100%.

A17

The injectable composition of example A15 or A16, wherein the injectable composition has mole fractions of the end groups that possess a hydrolysable moiety and cross linkable moiety in the range of about 20% to 80%.

A18

The injectable composition of one or more of examples A1 to A17, wherein the hydrolytically sensitive siloxane moiety is capable upon contact with moisture to generate one or more reactive silanol groups and hydrolysis products.

A19

The injectable composition of example A18, wherein the injectable composition is substantially cured through condensation of one or more reactive silanol groups.

A20

The injectable composition of example A19, wherein the injectable composition is capable of being substantially cured and the substantially cured composition has a refractive index in the range of about 1.4 to about 1.5.

A21

The injectable composition of example A20, wherein the injectable composition is capable of being substantially cured and the substantially cured composition has a refractive index in the range of about 1.41 to about 1.45.

A22

The injectable composition of examples A20 or A21 wherein the injectable composition is capable of being substantially cured and the substantially cured composition has a refractive index in the range of about 1.42 to about 1.44.

A23

The injectable composition of one or more of examples A20 to A22, wherein the injectable composition is capable of being substantially cured and the substantially cured composition has a refractive index of at least 1.4.

A24

The injectable composition of one or more of examples A19 to A23, wherein the injectable composition is capable of being substantially cured and the substantially cured composition has a modulus of elasticity of about 6 kPa or less.

A25

The injectable composition of examples A24, wherein the injectable composition is capable of being substantially cured and the substantially cured composition has a modulus of elasticity of about 0.1 to about 4 kPa.

A26

The injectable composition of example A24 or A25, wherein the injectable composition is capable of being substantially cured and the substantially cured composition has a modulus of elasticity of about 0.1 to about 2 KPa.

A27

The injectable composition of one or more of examples A24 to A26, wherein the injectable composition is capable of being substantially cured and the substantially cured composition has a modulus of elasticity of at least 0.1 kPa.

A28

The injectable composition of one or more of examples A19 to A27, wherein the injectable composition is capable of being substantially cured and the substantially cured composition has a dioptric range of accommodation of 0D to 10D.

A29

The injectable composition of example A28, wherein the injectable composition is capable of being substantially cured and the substantially cured composition has a dioptric range of accommodation of about 0D to about 6D.

A30

The injectable composition of example A28 or A29, wherein the injectable composition is capable of being substantially cured and the substantially cured composition has a dioptric range of accommodation of about 0D to about 4D.

A31

The injectable composition of one or more of examples A19 to A30, wherein the injectable composition is capable of being substantially cured and the substantially cured composition has extractables less than about 20%.

A32

The injectable composition of one or more of example A31, wherein the injectable composition is capable of being substantially cured and the substantially cured composition has extractables of about 0.5% to about 18%.

A33

The injectable composition of examples A31 or A32, wherein the injectable composition is capable of being substantially cured and the substantially cured composition has extractables of about 0.5% to about 16%.

A34

The injectable composition of one or more of examples A31 to A33, wherein the injectable composition is capable of being substantially cured and the substantially cured composition has extractables of about 0.5% to about 10%.

A35

The injectable composition of one or more of examples A31 to A34, wherein the injectable composition is capable of being substantially cured and the substantially cured composition has extractables of about 1% to about 5%.

A36

A method of making an injectable composition for forming an accommodating intraocular lens in situ, comprising the step of mixing together
   an organosilicon compound and
   a hydrolytically sensitive siloxane moiety
   wherein the mixing together is performed using catalytic hydrosilation or condensation to form the injectable composition.

A37

The method of example A36, wherein the organosilicon compound comprises linear polysiloxane polymer chains, linear poly siloxane copolymer chains, branched polysiloxane polymer chains, or combinations thereof.

A38

The method of example A36, wherein the wherein the hydrolytically sensitive siloxane moiety comprises one or more of silane ether groups and/or one of more groups of silane ester groups.

A39

The method of example A36, wherein the catalytic hydrosilylation is performed with one or more of catalysts comprising chloroplatinic acid, Karstedt's catalyst, Palladium acetate and Platinum oxide.

A40

The method of example A36, wherein the condensation is performed with a polyfunction silyl ester and/or silyl ether monomers.

A41

An intraocular lens formed in situ by the steps comprising:
a) injecting a composition comprising an organosilicon compound and a hydrolytically sensitive siloxane moiety into a capsule and
b) allowing the composition to cure upon contact with moisture, water or an aqueous medium to form the intraocular lens.

A42

The intraocular lens of example A41, wherein the organosilicon compound comprises linear polydimethylsiloxane polymer chains, linear poly siloxane copolymer chains, branched polysiloxane polymer chains, or combinations thereof

A43

The intraocular lens of examples A41 or A42, wherein the intraocular lens is suitably transparent.

A44

The intraocular lens of examples A41 to A43, wherein the intraocular lens has a refractive index in the range of about 1.4 to 1.5.

A45

The intraocular lens of example A44, wherein the intraocular lens has a refractive index in the range of 1.41 to 1.45.

A46

The intraocular lens of examples A44 or A45, wherein the intraocular lens has a refractive index in the range of about 1.42 to 1.44.

A47

The intraocular lens of examples A41 to A46, wherein the intraocular lens has a modulus of elasticity of about 6 kPa or less.

A48

The intraocular lens of example A47, wherein the intraocular lens has a modulus of elasticity of about 0.1 to 4 kPa.

A49

The intraocular lens of examples A47 or A48, wherein the intraocular lens has a modulus of elasticity of about 0.1 to 2 kPa.

A50

The intraocular lens of examples A41 to A49, wherein the intraocular lens has a dioptric range of accommodation of up to 10D.

A51

The intraocular lens of example A50, wherein the intraocular lens has a dioptric range of accommodation of about 0D to 6D.

A52

The intraocular lens of examples A50 or A51, wherein the intraocular lens has a dioptric range of accommodation of about 0D to 4D.

A53

The intraocular lens of examples A41 to A52, wherein the composition is injected using a injecting device.

A54

A method of forming an intraocular lens in situ, by the steps comprising:
a) injecting a composition comprising an organosilicon compound and a hydrolytically sensitive siloxane moiety into a capsule and
b) allowing the composition to substantially cure upon contact with moisture, water or an aqueous medium to form the intraocular lens.

A55

A method according to example A54, wherein the composition is injected using an injection device.

A56

A method according to example A54, wherein the composition is substantially cured to form the intraocular lens from within about 30 minutes to 7 days.

A57

A method according to examples A54 to A56, wherein the intraocular lens has a modulus of elasticity of about 6 kPa or less.

A58

A method according to example A57, wherein the intraocular lens has a modulus of elasticity of about 0.1 to 4 kPa.

A59

A method according to examples A57 or A58, wherein the intraocular lens has a modulus of elasticity of about 0.1 to 2 kPa.

A60

A method according to examples A54 to A59, wherein the intraocular lens has a refractive index in the range of about 1.4 to 1.5.

A61

A method according to example A60, wherein the intraocular lens has a refractive index in the range of 1.41 to 1.45.

A62

A method according to examples A60 or A61, wherein the intraocular lens has a refractive index in the range of about 1.42 to 1.44.

A63

A method according to examples A54 to A62, wherein the intraocular lens has a dioptric range of accommodation of 0D to 10D.

A64

A method according to example A63, wherein the intraocular lens has a dioptric range of accommodation of about 0D to 6D.

A65

A method according to examples A63 or A64, wherein the intraocular lens has a dioptric range of accommodation of about 0D to 4D.

A66

A kit comprising one or more of
an injectable composition comprising an organosilicon compound and a hydrolytically sensitive siloxane moiety and having a specific gravity greater than 0.95, a number average molecular weight ($M_n$) greater than about 5,000 and a weight average molecular weight ($M_w$) greater than about 20,000;
an injection device; or
a valve device for sealing the aperture on the surface of the capsular bag of the eye.

A67

An accommodating intraocular lens formed in situ in the capsule by moisture cure of an organosilicon compound and a hydrolytically sensitive siloxane moiety and having one or more properties comprising:
i) an elastic modulus of about 6 kPa or less;
ii) less than about 20% of post-cure extractables;
iii) a refractive index in the range of about 1.4 to about 1.5; or
iv) a dioptric range of accommodation of 0 to 10D.

A68

The intraocular lens of example A67, wherein at least 50% of the post-cure extractables have a number average molecular weight ($M_n$) of greater than about 30,000.

What is claimed is:

1. An injectable composition for forming an accommodating intraocular lens in situ in a capsule, comprising:
   a siloxane polymer derived from an organosilicon compound and a compound having a hydrolytically sensitive siloxane moiety,
   wherein the injectable composition has a specific gravity in the range of 1 to 1.04 and is capable of being substantially cured in situ upon contact with moisture; and
   wherein the siloxane polymer has a number average molecular weight ($M_n$) greater than about 5,000, and a weight average molecular weight ($M_w$) greater than about 20,000.

2. The injectable composition of claim 1, wherein the organosilicon compound comprises linear polysiloxane polymer chains, linear poly siloxane copolymer chains, branched polysiloxane polymer chains, or combinations thereof.

3. The injectable composition of claim 1, wherein the hydrolytically sensitive siloxane moiety comprises one or more of silane ether groups and/or one of more groups of silane ester groups.

4. The injectable composition of claim 1, wherein the number average molecular weight ($M_n$) is in the range of about 5,000 to 150,000.

5. The injectable composition of claim 1, wherein the weight average molecular weight ($M_w$) is in the range of about 20,000 to 300,000.

6. The injectable composition of claim 1, wherein the injectable composition has mole fractions of the end groups that possess a hydrolysable moiety and cross linkable moiety in the range of greater than about 20%.

7. The injectable composition of claim 1, wherein the injectable composition is substantially cured through condensation of one or more reactive silanol groups.

8. The injectable composition of claim 1, wherein the injectable composition is capable of being substantially cured and the substantially cured composition has a refractive index in the range of about 1.41 to about 1.45.

9. The injectable composition of claim 1, wherein the injectable composition is capable of being substantially cured and the substantially cured composition has a refractive index of at least 1.4.

10. The injectable composition of claim 1, wherein the injectable composition is capable of being substantially cured and the substantially cured composition has a modulus of elasticity of about 0.1 to about 4 kPa.

11. The injectable composition of claim 1, wherein the injectable composition is capable of being substantially cured and the substantially cured composition has a dioptric range of accommodation of 0D to 10D.

* * * * *